United States Patent
Matsuo et al.

(10) Patent No.: US 8,034,934 B2
(45) Date of Patent: Oct. 11, 2011

(54) PROCESS FOR PRODUCING ORTHO-METALATED COMPLEX OF IRIDIUM WITH HOMOLIGAND

(75) Inventors: Shinji Matsuo, Fukuoka (JP); Hiromi Hashimoto, Fukuoka (JP); Kazuo Ishii, Fukuoka (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 878 days.

(21) Appl. No.: 11/991,529

(22) PCT Filed: Aug. 29, 2006

(86) PCT No.: PCT/JP2006/316926
§ 371 (c)(1),
(2), (4) Date: Mar. 6, 2008

(87) PCT Pub. No.: WO2007/032203
PCT Pub. Date: Mar. 22, 2007

(65) Prior Publication Data
US 2008/0255361 A1    Oct. 16, 2008

(30) Foreign Application Priority Data
Sep. 12, 2005   (JP) ................. 2005-263538

(51) Int. Cl.
*C07F 15/00* (2006.01)
(52) U.S. Cl. ................. 546/2; 546/10; 548/108
(58) Field of Classification Search ............ 546/2, 10; 548/108
See application file for complete search history.

(56) References Cited

U.S. PATENT DOCUMENTS

| | | | |
|---|---|---|---|
| 7,084,273 B2 * | 8/2006 | Stossel et al. | 546/4 |
| 2004/0077862 A1 | 4/2004 | Stossel et al. | |
| 2005/0002485 A1 | 1/2005 | Matsumura et al. | |
| 2005/0131232 A1 | 6/2005 | Stossel et al. | |

FOREIGN PATENT DOCUMENTS

| | | |
|---|---|---|
| JP | 2001-247859 A | 9/2001 |
| JP | 2003-81988 A | 3/2003 |
| JP | 2004-168755 A | 6/2004 |
| JP | 2004-168758 A | 6/2004 |
| JP | 2004-337802 A | 12/2004 |
| WO | WO-01/41512 A1 | 6/2001 |
| WO | WO-03/099959 A1 | 12/2003 |

OTHER PUBLICATIONS

Inorg. Chem., 1991, vol. 30, pp. 1685-1687.
King et al., J. Am. Chem. Soc., 1985, vol. 107, pp. 1431-1432.
Thompson et al., High Efficiency Organic Electrophosporescent Devices, Proc. SPIE, vol. 4105, (2001), pp. 119-124.
Lamansky et al., J. Am. Chem., 2001, vol. 123, pp. 4304-4312.

* cited by examiner

*Primary Examiner* — Charanjit Aulakh
(74) *Attorney, Agent, or Firm* — Birch, Stewart, Kolasch & Birch, LLP

(57) ABSTRACT

Disclosed is a process for producing an ortho-metalated 1:3 complex of iridium with homoligands which is useful as a luminous material for an organic EL device in high yield at high purity in a short time by a simple procedure. An example of the complex is tris(2-phenylpyridine)iridium(III) and this complex can be produced by reacting iridium(III) acetylacetonate with an organic ligand consisting of 2-phenylpyridine in the copresence of an acidic substance, either an organic acid such as tartaric acid or an inorganic acid such as phosphoric acid.

12 Claims, No Drawings

PROCESS FOR PRODUCING ORTHO-METALATED COMPLEX OF IRIDIUM WITH HOMOLIGAND

FIELD OF TECHNOLOGY

This invention relates to a process for producing an ortho-metalated complex of iridium with homoligands (hereinafter also referred to as iridium complex) which is useful as a luminous material for an organic EL device.

BACKGROUND TECHNOLOGY

An organic EL device emits light of high brightness at low voltage and, on account of this ability, it has attracted attention as a promising display device while creating an increasing demand for enhanced brightness. Of such promising materials, an ortho-metalated iridium complex, represented by tris(2-phenylpyridine)iridium complex, is attracting particular attention as it is capable of emitting light from the triplet excited state thereby producing higher quantum efficiency compared with the conventional emission of light utilizing phosphorescence. Furthermore, in recent years, developmental works focused on furnishing ortho-metalated iridium complexes with high color purity, high efficiency, and long service life required for loading into practical devices are gaining force and there is a strong demand for a process capable of producing the desired complexes in a higher yield by a simpler procedure.

The prior-art documents relating to this invention are listed below.

Patent document 1: US2004/0077862 A1
Patent document 2: WO01/41512 A
Patent document 3: JP2003-81988 A
Patent document 4: JP2001-247859 A
Patent document 5: JP2004-168755 A
Patent document 6: JP2004-168758 A
Non-patent document 1: Inorganic Chemistry, 30, 1685 (1991)
Non-patent document 2: Journal of the American Chemical Society, 107, 1431 (1958)
Non-patent document 3: Proceeding of SPIE, 4105,119 (2001)
Non-patent document 4: Journal of the American Chemical Society, 123, 4303 (2001)

For the synthesis of ortho-metalated iridium complexes, the process described in the non-patent document 1 starts from iridium(III) acetylacetonate while the process in the non-patent document 2 starts from iridium(III) chloride. However, these processes give the complexes in low yield. The non-patent document 3 describes the extreme difficulty of synthesizing ortho-metalated complexes of iridium with homoligands from most of the ligands when the process starting from iridium(III) acetylacetonate is used.

A variety of ortho-metalated iridium complexes are synthesized from iridium(III) acetylacetonate in the patent documents 2 and 3 or from $K_3IrCl_6$ in the patent document 4. However, the yields are extremely low, ranging from 3 to 40%, in all the examples described in these documents.

The yields range from 62 to 65% in the patent document 5 wherein iridium(III) chloride is used as a staring material and the ligand is used in large excess, more than 30 times that of iridium(III) chloride in terms of equivalent, or the yield is 60% in the patent document 6 wherein a basic substance is allowed to be present in the system. However, the yields here are not sufficiently high and, besides, the use of iridium(III) chloride poses problems such as formation of difficultly separable byproducts and residual chlorine.

On the other hand, the patent document 1 gives an account of optimizing the conditions of the method described in the non-patent document 1, that is, the method which uses iridium(III) acetylacetonate as a raw material. According to this account, the ortho-metalated iridium complexes are obtained in a yield as high as 90% or more by carrying out the reaction in a polar solvent for 20 to 60 hours while setting the ratio of raw materials in a specific range and performing the acid washing as an after-treatment. However, the inventors of this invention confirmed that the ortho-metalated iridium complexes in question were difficult to obtain in such a high yield of 90% or more, although the yield improved a little over the one described in the non-patent document 1.

DISCLOSURE OF THE INVENTION

Problems to be Solved by the Invention

An object of this invention is to provide a process for producing an ortho-metalated complex of iridium with homoligands in high yield at high purity in a short period of time by a simple procedure.

Means to Solve the Problems

The inventors of this invention have conducted studies to solve the aforementioned problems, and have found that allowing an acidic substance to coexist in the reaction can accelerate the reaction and improve the yield, thereby completing the invention.

This invention relates to a process for producing an ortho-metalated iridium complex comprising the reaction of iridium(III) acetylacetonate with an organic ligand to give an ortho-metalated complex of iridium with homoligands (preferably a 1:3 complex of iridium with homoligands) wherein the said reaction is carried out in the copresence of an acidic substance.

An ortho-metalated iridium complex is represented by the following general formula (1)

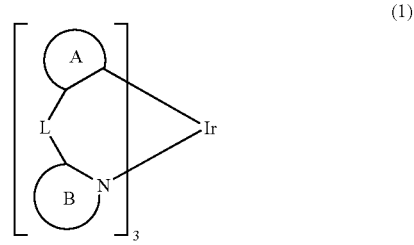

(1)

wherein ring A denotes a 5- or 6-membered aromatic or aromatic hetero ring, either unsubstituted or substituted, ring B denotes a nitrogen-containing 5- or 6-membered hetero ring, either unsubstituted or substituted, any adjacent substituents on ring A or ring B may join together to form a condensed ring, L is a single bond or a divalent group, and L, ring A, ring B, and any substituents thereon may join together to form a condensed ring involving ring A and ring B.

In general formula (1), preferable examples of ring B include the rings of pyridine, pyrimidine, pyrazine, pyridazine, pyrrole, quinoline, isoquinoline, imidazole, pyrazole, thiazole, oxazole, oxadiazole, thiadiazole, 1,2,3-triazole, 1,2,4-triazole, benzothiazole, benzoxazole, and benzimidazole, either unsubstituted or substituted. Preferable examples of ring A include the rings of imidazole, thiazole, oxazole, pyrrole, oxadiazole, thiadiazole, pyrazole, 1,2,3-triazole, 1,2,4-triazole, selenazole, furan, thiophene, benzene, naphthalene, phenanthrene, pyridine, pyrimidine, pyrazine, and pyridazine, either unsubstituted or substituted.

A preferable example of the acidic substances is a Bronsted acid and a preferable example of the ortho-metalated iridium complexes is an ortho-metalated 1:3 complex of iridium with homoligands.

The reaction in the copresence of an acidic substance is preferably carried out at a temperature in the range of 150 to 220° C. or in the presence of at least one kind of solvent selected from polyhydric alcohols, esters of polyhydric alcohols, ethers of polyhydric alcohols, and aliphatic hydrocarbons.

The organic ligands useful for this invention are not limited as long as they can be used as reactants of this kind, but it is necessary to use a multidentate ligand which is capable of forming at least one ortho-metalated coordinate bond consisting of an iridium-nitrogen bond and an iridium-carbon bond.

Examples of the ligands capable of forming such an ortho-metalated coordinate bond include 2-phenylpyridine, 2-phenylquinoline, 7,8-benzoquinoline, 2-(2-thienyl)pyridine, 1-phenylpyrazole, 2-phenylisoquinoline, 2-(2-benzothiophenyl)pyridine, 2-benzylpyridine, and 2-(1-naphthyl)pyridine and further include those derivatives of the foregoing compounds which have substituents on ring carbon atoms and the organic ligands described in the patent documents 1 to 6 and the non-patent documents 1 to 4.

The preferable organic ligands are those which give the ortho-metalated iridium complexes represented by general formula (1). The organic ligands of this kind have a structure yielding ring A, ring B, and L in general formula (1) and, normally, the ring to yield ring A has one more hydrogen atom.

In general formula (1), ring A is preferably a 5- or 6-membered aromatic or aromatic hetero ring, either unsubstituted or substituted, while ring B is preferably a nitrogen-containing 5- or 6-membered hetero ring, either unsubstituted or substituted.

Examples of the substituent groups on ring A or ring B include alkyl, substituted alkyl, alkenyl, substituted alkenyl, phenoxy, substituted phenoxy, aryl, substituted aryl, aralkyl, substituted aralkyl, alkoxy, substituted alkoxy, dialkylamino, and substituted dialkylamino and preferable are alkyl groups of 1 to 10 carbon atoms, substituted alkyl groups of 1 to 10 carbon atoms, alkenyl groups of 1 to 10 carbon atoms, aryl groups of 6 to 10 carbon atoms, substituted aryl groups of 6 to 10 carbon atoms, aralkyl groups of 6 to 12 carbon atoms, substituted aralkyl groups of 6 to 12 carbon atoms, alkoxy groups of 1 to 10 carbon atoms, and substituted alkoxy groups of 1 to 10 carbon atoms. Of the substituents on ring A or ring B, those which are located adjacent to each other may join together to form a condensed ring.

Preferable examples of the aromatic rings or aromatic hetero rings, either unsubstituted or substituted, for constituting ring A include the rings of imidazole, thiazole, oxazole, pyrrole, oxadiazole, thiadiazole, pyrazole, 1,2,3-triazole, 1,2,4-triazole, selenazole, furan, thiophene, benzene, naphthalene, phenanthrene, pyridine, pyrimidine, pyrazine, and pyridazine.

Preferable examples of the nitrogen-containing hetero rings, either unsubstituted or substituted, for constituting ring B include the rings of pyridine, pyrimidine, pyrazine, pyridazine, pyrrole, quinoline, isoquinoline, imidazole, pyrazole, thiazole, oxazole, oxadiazole, thiadiazole, 1,2,3-triazole, 1,2,4-triazole, benzothiazole, benzoxazole, and benzimidazole.

The group L denotes a single bond or a divalent group and it is preferably a single bond, —C(R1)(R2)—, —N(R3)—, —O—, or —S—. The groups R1 and R2 here independently denote a hydrogen atom, aliphatic group of 1 to 6 carbon atoms, aromatic group of 12 or less carbon atoms, cyano group, or nitro group. The group R3 denotes an aliphatic group, aromatic group, or heterocyclic group. The group L, ring A, ring B, and any substituents thereon may join together to form a condensed ring involving ring A and ring B.

The molar ratio of the organic ligand to iridium(ill) acetonate should be controlled at 3:1 or higher, preferably 3:1 to 36:1. When the molar ratio is less than 3:1, the exchange of ligand takes place insufficiently and the yield of an ortho-metalated iridium complex drops. When the molar ratio is more than 3:1, there is no restriction on the amount used, but the use of more than is necessary is economically inefficient.

The acidic substance to be used in this invention may be any compound which can act as a source of proton in the reaction system or which can accept a pair of electrons such as a Lewis acid and a solid acid. A Bronsted acid is preferable and its examples include organic acids such as acetic acid, oxalic acid, valeric acid, butyric acid, and tartaric acid and inorganic acids such as hydrochloric acid, sulfuric acid, and phosphoric acid. These acids may be used singly or as a mixture of two kinds or more. When any of the acidic substances in use has a boiling point lower than the reaction temperature, it boils under reflux to prevent the reaction system from rising to a temperature sufficiently high to advance the reaction. Hence, the acidic substance preferably has a boiling point of 150° C. or above.

The molar ratio of the acidic substance to iridium(III) acetonate is 0.5:1 or more, preferably 0.5:1 to 20:1, more preferably 3:1 to 20:1. A molar ratio of less than 0.5:1 is undesirable because the reaction cannot be accelerated sufficiently and the reaction cannot be completed in a short time. A molar ratio of more than 0.5:1 does not restrict the amount of use, but the use of more than is necessary is economically inefficient.

The reaction temperature in this invention ranges from 150 to 220° C., preferably from 180 to 210° C. The reaction hardly proceeds below 150° C. while more byproducts form above 220° C.

The reaction time in this invention ranges from 1 to 80 hours, preferably from 2 to 30 hours, although it varies with the reaction conditions. The reaction is preferably carried out in an nitrogen or argon atmosphere.

It is allowable to use a solvent as needed in this invention. Any solvent which does not participate in the reaction or does not hinder the reaction may be used advantageously and a solvent boiling above the reaction temperature is desirable as there is no need for pressurizing. A preferred solvent is at least one kind selected from polyhydric alcohols, esters of polyhydric alcohols, ethers of polyhydric alcohols, and aliphatic hydrocarbons, all boiling above 150° C., preferably above 180° C. The solvents of this kind include polyhydric alcohols such as ethylene glycol, propylene glycol, glycerin, diethylene glycol, PEG600, and PEG1000, esters of polyhydric alcohols such as ethylene glycol diacetate, ethylene glycol dibutyrate, ethylene glycol monobutyl ether acetate, and glycerol monoacetate, ethers of polyhydric alcohols such as triethylene glycol dimethyl ether and polyethylene glycol dimethyl ether, and aliphatic hydrocarbons such as bicyclohexyl, decahydronaphthalene, 1-methyldecahydronaphthalene, spiro(5,5)undecane, and tetradecahydrophenanthrene.

In this invention, the yield or reaction rate improves in the presence of an acidic substance probably for the following reason. According to the reaction mechanism involved in the synthesis of an ortho-metalated iridium complex using iridium(III) acetylacetonate as a raw material, the nitrogen atom of the ligand (for example, 2-phenylpyridine) nucleophilically attacks the iridium metal to form a coordinate bond and then a carbon-iridium covalent bond forms accompanied by the dehydrogenation step. The rate-determining step of this complex formation seems to be the nucleophilic attack by the nitrogen atom of the ligand and the electron density over the nitrogen atom and the steric bulkiness around the nitrogen atom affect the reaction rate greatly and make the synthesis of various derivatives difficult. For example, in the case where 2-phenylisoquinoline, 2-benzoxazole, or 2-benzothioxazole is used as a ligand in place of 2-phenylpyridine, the electron density over the nitrogen atom becomes delocalized over the whole condensed aromatic ring to lower the ability of nucleophilic attack and, as a result, a phenomenon of excessive drop of the reaction yield is observed.

Under the aforementioned circumstances, the inventors of this invention have inferred that an acidic substance coexisting in the said reaction protonates the oxygen atom of the acetylacetone ligand on the starting material iridium(III) acetylacetonate to accelerate the cleavage of the oxygen-iridium covalent bond and facilitate the nucleophilic attack by the nitrogen atom of the ligand.

Representative examples of the ortho-metalated iridium complexes to be produced by this invention are listed below, but this invention is not limited to these examples.

(2)

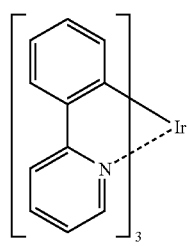

(3)

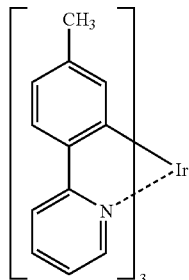

(4)

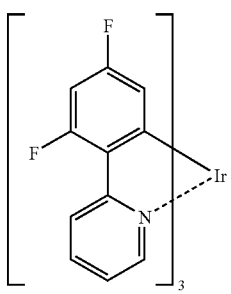

(5)

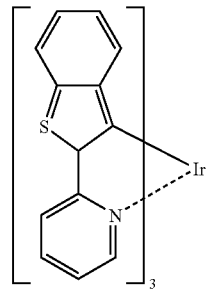

(6)

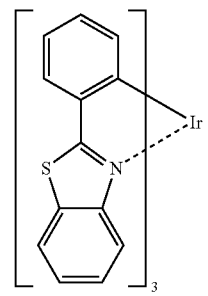

(7)

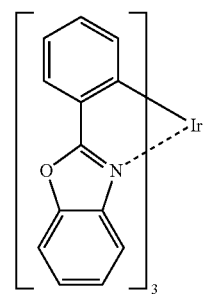

(8)

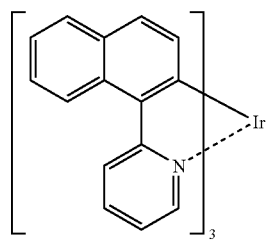

(9)

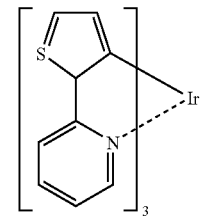

(10)

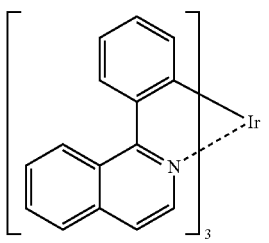

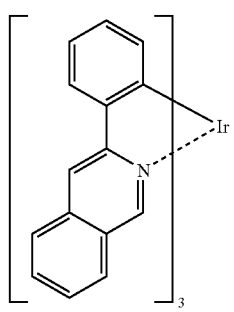 (11)

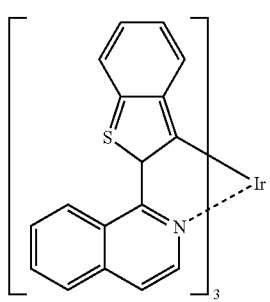 (12)

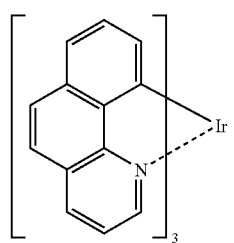 (13)

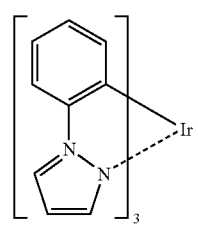 (14)

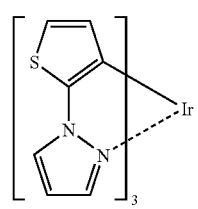 (15)

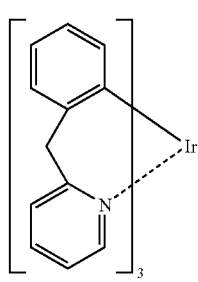 (16)

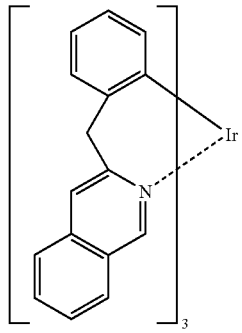 (17)

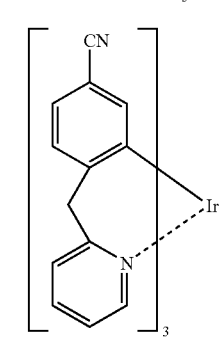 (18)

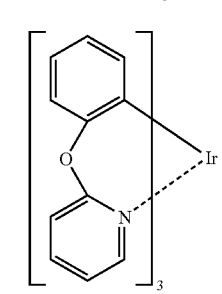 (19)

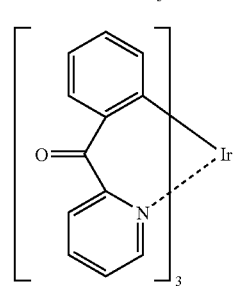 (20)

PREFERRED EMBODIMENTS OF THE INVENTION

This invention will be described in more detail below with reference to the examples, but is not limited to these examples.

The compound number of the ortho-metalated iridium complex described in the example corresponds to the number used in the aforementioned list of representative examples.

EXAMPLE 1

In a three-necked flask equipped with a reflux condenser was placed 100 ml of glycerin and the flask was swept free of air by blowing $N_2$ for 3.5 hours. Thereafter, 2.0 g of iridium (III) acetylacetonate, 7.5 g of 2-phenylpyridine, and 3.3 g of tartaric acid were added and, in a nitrogen atmosphere, the mixture was heated under reflux in an oil bath at a bath temperature of 200-210° C. with stirring for 10 hours. Upon completion of the reaction, the mixture was cooled to room temperature, 30 ml of ethanol and 300 ml of 2N HCl were added, the mixture was stirred, and the precipitate was filtered. The precipitate was transferred to a beaker, washed with 50 ml of ethanol with stirring, and filtered again. The precipitate thus obtained was transferred to a 100-ml eggplant-shaped flask, 60 ml of acetonitrile was added, and the mixture was heated with stirring in an oil bath at a bath temperature of 100° C. for 1 hour. The mixture was cooled to room temperature and the precipitate was filtered, washed with 30 ml of acetonitrile and 30 ml of ethanol, and dried under reduced pressure at 80° C. for 5 hours to give 1.8 g of yellow crystals. An MS analysis identified the yellow crystal as tris(2-phenylpyridine)iridium(III) or ortho-metalated iridium complex (2) represented by chemical formula (2): yield, 68%; purity by HPLC, 99%; MS (ESI-TOFMS), 655.

EXAMPLE 2

In a three-necked flask equipped with a reflux condenser was placed 100 ml of glycerin and the flask was swept free of air by blowing $N_2$ for 3.5 hours. Thereafter, 2.0 g of iridium (III) acetylacetonate, 7.5 g of 2-phenylpyridine, and 3.3 g of tartaric acid were added and, in a nitrogen atmosphere, the mixture was heated under reflux in an oil bath at a bath temperature of 200-210° C. with stirring for 44 hours. Upon completion of the reaction, the mixture was cooled to room temperature, 30 ml of ethanol and 300 ml of 2N HCl were added, the mixture was stirred, and the precipitate was filtered. The precipitate was transferred to a beaker, washed with 50 ml of ethanol with stirring, and filtered again. The precipitate thus obtained was transferred to a 100-ml eggplant-shaped flask, 60 ml of acetonitrile was added, and the mixture was heated with stirring in an oil bath at a bath temperature of 100° C. for 1 hour. The mixture was cooled to room temperature and the precipitate was filtered, washed with 30 ml of acetonitrile and 30 ml of ethanol, and dried under reduced pressure at 80° C. for 5 hours to give 2.2 g of yellow crystals. An MS analysis identified the yellow crystal as ortho-metalated iridium complex (2): yield, 83%; purity by HPLC, 99%; MS (ESI-TOFMS), 655.

EXAMPLE 3

In a three-necked flask equipped with a reflux condenser was placed 100 ml of glycerin and the flask was swept free of air by blowing with $N_2$ for 3.5 hours. Thereafter, 2.0 g of iridium(III) acetylacetonate, 7.5 g of 2-phenylpyridine, and 9 g of tartaric acid were added and, in a nitrogen atmosphere, the mixture was heated under reflux in an oil bath at a bath temperature of 200-210° C. with stirring for 5 hours. Upon completion of the reaction, the mixture was cooled to room temperature, 30 ml of ethanol and 300 ml of 2N HCl were added, the mixture was stirred, and the precipitate was filtered. The precipitate was transferred to a beaker, washed with 50 ml of ethanol with stirring, and filtered again. The precipitate thus obtained was transferred to a 100-ml eggplant-shaped flask, 60 ml of acetonitrile was added, and the mixture was heated in an oil bath at a bath temperature of 100° C. for 1 hour. The mixture was cooled to room temperature and the precipitate was filtered, washed with 30 ml of acetonitrile and 30 ml of ethanol, and dried under reduced pressure at 80° C. for 5 hours to give 1.8 g of yellow crystals. An MS analysis identified the yellow crystal as ortho-metalated iridium complex (2): yield, 70%; purity by HPLC, 99%; MS (ESI-TOFMS), 655.

EXAMPLE 4

In a three-necked flask equipped with a reflux condenser was placed 100 ml of glycerin and the flask was swept free of air by blowing $N_2$ for 3.5 hours. Thereafter, 2.0 g of iridium (III) acetylacetonate, 7.5 g of 2-phenylpyridine, and 9 g of tartaric acid were added and, in a nitrogen atmosphere, the mixture was heated under reflux in an oil bath at a bath temperature of 200-210° C. with stirring for 10 hours. Upon completion of the reaction, the mixture was cooled to room temperature, 30 ml of ethanol and 300 ml of 2N HCl were added, the mixture was stirred, and the precipitate was filtered. The precipitate was transferred to a beaker, washed with 50 ml of ethanol with stirring, and filtered again. The precipitate thus obtained was transferred to a 100-ml eggplant-shaped flask, 60 ml of acetonitrile was added, and the mixture was heated in an oil bath at a bath temperature of 100° C. for 1 hour. The mixture was cooled to room temperature and the precipitate was filtered, washed with 30 ml of acetonitrile and 30 ml of ethanol, and dried under reduced pressure at 80° C. for 5 hours to give 2.2 g of yellow crystals. An MS analysis identified the yellow crystal as ortho-metalated iridium complex (2): yield, 85%; purity by HPLC, 99%; MS (ESI-TOFMS), 655.

EXAMPLE 5

In a three-necked flask equipped with a reflux condenser was placed 100 ml of glycerin and the flask was swept free of air by blowing $N_2$ for 3.5 hours. Thereafter, 2.0 g of iridium (III) acetylacetonate, 7.5 g of 2-phenylpyridine, and 5.9 g of phosphoric acid (85% aqueous solution) were added and, in a nitrogen atmosphere, the mixture was heated -under reflux in an oil bath at a bath temperature of 200-210° C. with stirring for 10 hours. Upon completion of the reaction, the mixture was cooled to room temperature, 30 ml of ethanol and 300 ml of 2N HCl were added, the mixture was stirred, and the precipitate was filtered. The precipitate was transferred to a beaker, washed with 50 ml of ethanol with stirring, and filtered again. The precipitate thus obtained was transferred to a 100-ml eggplant-shaped flask, 60 ml of acetonitrile was added, and the mixture was heated in an oil bath at a bath temperature of 100° C. for 1 hour. The mixture was cooled to room temperature and the precipitate was filtered, washed with 30 ml of acetonitrile and 30 ml of ethanol, and dried under reduced pressure at 80° C. for 5 hours to give 2.4 g of yellow crystals. An MS analysis identified the yellow crystal as ortho-metalated iridium complex (2): yield, 92%; purity by HPLC, 99%; MS (ESI-TOFMS), 655.

EXAMPLE 6

In a three-necked flask equipped with a reflux condenser was placed 200 ml of glycerin and the flask was swept free of air by blowing $N_2$ for 3.5 hours. Thereafter, 3.0 g of iridium (III) acetylacetonate, 7.6 g of 2-(pyridin-2-yl)benzo[b]thiophene, and 8.8 g of phosphoric acid (85% aqueous solution) were added and, in a nitrogen atmosphere, the mixture was heated under reflux in an oil bath at a bath temperature of 200-210° C. with stirring for 7 hours. Upon completion of the reaction, the mixture was cooled to room temperature, 45 ml of ethanol and 450 ml of 2N HCl were added, the mixture was stirred, and the precipitate was filtered. The precipitate was transferred to a beaker, washed with 75 ml of ethanol with stirring, and filtered again. The precipitate thus obtained was transferred to a 200-ml eggplant-shaped flask, 90 ml of acetonitrile was added, and the mixture was heated in an oil bath at a bath temperature of 100° C. for 1 hour. The mixture was cooled to room temperature and the precipitate was filtered, washed with 45 ml of acetonitrile and 45 ml of ethanol, and dried under reduced pressure at 80° C. for 5 hours to give 4.32 g of reddish orange crystals. An MS analysis identified the reddish orange crystal as tris[2-(pyridin-2-yl)benzo[b] thiophene]iridium(III) or ortho-metalated iridium complex (5): yield, 86%; purity by HPLC, 99%; MS (ESI-TOFMS), 826.

COMPARATIVE EXAMPLE 1

In a three-necked flask equipped with a reflux condenser was placed 100 ml of glycerin and the flask was swept free of air by blowing $N_2$ for 3.5 hours. Thereafter, 2.0 g of iridium (III) acetylacetonate and 7.5 g of 2-phenylpyridine were added and, in a nitrogen atmosphere, the mixture was heated under reflux in an oil bath at a bath temperature of 200-210° C. with stirring for 44 hours. Upon completion of the reaction, the mixture was cooled to room temperature, 30 ml of ethanol and 300 ml of 2N HCl were added, the mixture was stirred, and the precipitate was filtered. The precipitate was transferred to a beaker, washed with 50 ml of ethanol with stirring, and filtered again. The precipitate thus obtained was transferred to a 100-ml eggplant-shaped flask, 60 ml of acetonitrile was added, and the mixture was heated in an oil bath at a bath temperature of 100° C. for 1 hour. The mixture was cooled to room temperature and the precipitate was filtered, washed with 30 ml of acetonitrile and 30 ml of ethanol, and dried under reduced pressure at 80° C. for 5 hours to give 1.6 g of yellow crystals. An MS analysis identified the yellow crystal as ortho-metalated iridium complex (2): yield, 59%; purity by HPLC, 99%; MS (ESI-TOFMS), 655.

COMPARATIVE EXAMPLE 2

In a three-necked flask equipped with a reflux condenser was placed 50 ml of glycerin and the flask was swept free of air by blowing $N_2$ for 2 hours. Thereafter, 0.5 g of iridium(III) acetylacetonate and 0.9 g of 2-phenylpyridine were added and, in a nitrogen atmosphere, the mixture was heated under reflux in an oil bath at a bath temperature of 200-210° C. with stirring for 15 hours. Upon completion of the reaction, the mixture was cooled to room temperature, 300 ml of 1N HCl was added, and the precipitate was filtered. The precipitate was dissolved in 200 ml of dichloromethane by heating and then filtered. The filtrate was purified by silica gel column chromatography to give 0.2 g of yellow crystals. An MS analysis identified the yellow crystal as ortho-metalated iridium complex (2): yield, 28%; purity by HPLC, 99%; MS (ESI-TOFMS), 655.

COMPARATIVE EXAMPLE 3

In a three-necked flask equipped with a reflux condenser was placed 100 ml of ethylene glycol and the flask was swept free of air by blowing $N_2$ for 3.5 hours. Thereafter, 4.9 g of iridium(III) acetylacetonate and 15.5 g of 2-phenylpyridine were added and, in a nitrogen atmosphere, the mixture was heated under reflux in an oil bath at a bath temperature of 200-210° C. with stirring for 16 hours. Upon completion of the reaction, the mixture was cooled to room temperature, 200 ml of 1N HCl was added, the mixture was stirred for 5 minutes, and the precipitate was filtered. The precipitate thus obtained was washed three times with 30 ml of 1N HCl, then washed five times with 30 ml of water. The precipitate was dried at 80° C. for 5 hours and then at 200° C. under reduced pressure for 2 hours to give 2.3 g of yellow crystals. An MS analysis identified the yellow crystal as ortho-metalated iridium complex (2): yield, 35%; purity by HPLC, 99%; MS (ESI-TOFMS), 655.

COMPARATIVE EXAMPLE 4

The experiment was carried out as in Comparative Example 3 with the exception of heating under reflux with stirring for 42 hours. The yield of yellow crystals was 4.1 g and an MS analysis identified the yellow crystal as ortho-metalated iridium complex (2): yield, 62%; purity by HPLC, 97%; MS (ESI-TOFMS), 655.

INDUSTRIAL APPLICABILITY

An ortho-metalated complex of iridium with homoligands which has been considered difficult to produce in high yield in spite of its usefulness as a luminous material for an organic electroluminescent device can be produced in high yield at high purity in a short time by a simple procedure according to the process of this invention.

What is claimed is:

1. A process for producing an ortho-metalated iridium complex comprising the reaction of iridium(III) acetylacetonate with an organic ligand to produce an ortho-metalated complex of iridium with homoligands wherein the said reaction is carried out in the copresence of an acidic substance selected from Bronsted acids.

2. A process for producing an ortho-metalated iridium complex as described in claim 1 wherein the ortho-metalated complex of iridium with homoligands is a compound represented by the following general formula (1);

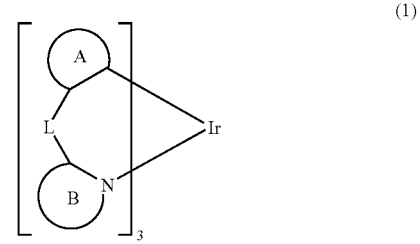

(1)

in the formula, ring A denotes a 5- or 6-membered aromatic or aromatic hetero ring, either unsubstituted or substituted, ring B denotes a nitrogen-containing 5- or 6-membered hetero ring, either unsubstituted or substituted, any adjacent substituents on ring A or ring B may join together to form a condensed ring, L denotes a single bond or a divalent group, and L, ring A, ring B, and any substituents thereon may join together to form a condensed ring involving ring A and ring B.

3. A process for producing an ortho-metalated iridium complex as described in claim 2 wherein ring B in general formula (1) is the ring of pyridine, pyrimidine, pyrazine, pyridazine, pyrrole, quinoline, isoquinoline, imidazole, pyrazole, thiazole, oxazole, oxadiazole, thiadiazole, 1,2,3-triazole, 1,2,4-triazole, benzothiazole, benzoxazole, or benzimidazole, either unsubstituted or substituted.

4. A process for producing an ortho-metalated iridium complex as described in claim 2 or 3 wherein ring A in general formula (1) is the ring of imidazole, thiazole, oxazole, pyrrole, oxadiazole, thiadiazole, pyrazole, 1,2,3-triazole, 1,2,4-triazole, selenazole, furan, thiophene, benzene, naphthalene, phenanthrene, pyridine, pyrimidine, pyrazine or pyridazine, either unsubstituted or substituted.

5. A process for producing an ortho-metalated iridium complex as described in claim 1 wherein the acidic substance is a Bronsted acid selected from organic acids and inorganic acids.

6. A process for producing an ortho-metalated iridium complex as described in claim 1 wherein the ortho-metalated iridium complex is an ortho-metalated 1:3 complex of iridium and homoligands.

7. A process for producing an ortho-metalated iridium complex as described in claim 1 wherein the reaction in the copresence of the acidic substance is carried out at a temperature in the range of 150 to 220° C.

8. A process for producing an ortho-metalated iridium complex as described in claim 1 wherein at least one kind of compound selected from polyhydric alcohols, esters of polyhydric alcohols, ethers of polyhydric alcohols, and aliphatic hydrocarbons is used as a solvent in the reaction.

9. A process for producing an ortho-metalated iridium complex as described in claim 1 wherein the reaction is carried out at a temperature in the range of 150 to 220° C. in the copresence of the acidic substance selected from Bronsted acids in such a manner as to control the molar ratio of the acidic substance to iridium(III) acetylacetonate in the range of 0.5 to 20.

10. A process for producing an ortho-metalated iridium complex as described in claim 1 wherein the ortho-metalated complex of iridium with homoligands is a compound represented by the following general formula (1);

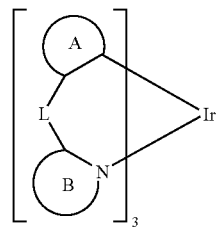

(1)

in the formula, ring A denotes an unsubstituted 5- or 6-membered aromatic or aromatic hetero ring, ring B denotes an unsubstituted nitrogen-containing 5- or 6-membered hetero ring, and L denotes a single bond or a divalent group.

11. A process for producing an ortho-metalated iridium complex as described in claim 2 wherein ring B in general formula (1) is an unsubstituted ring of pyridine, pyrimidine, pyrazine, pyridazine, pyrrole, quinoline, isoquinoline, imidazole, pyrazole, thiazole, oxazole, oxadiazole, thiadiazole, 1,2,3-triazole, 1,2,4-triazole, benzothiazole, benzoxazole, or benzimidazole.

12. A process for producing an ortho-metalated iridium complex as described in claim 2 or 3 wherein ring A in general formula (1) is an unsubstituted ring of imidazole, thiazole, oxazole, pyrrole, oxadiazole, thiadiazole, pyrazole, 1,2,3-triazole, 1,2,4-triazole, selenazole, furan, thiophene, benzene, naphthalene, phenanthrene, pyridine, pyrimidine, pyrazine or pyridazine.

* * * * *